US009399702B2

(12) United States Patent
Gaynor et al.

(10) Patent No.: US 9,399,702 B2
(45) Date of Patent: *Jul. 26, 2016

(54) CROSSLINKABLE ARYLAMINE COMPOUNDS AND CONJUGATED OLIGOMERS OR POLYMERS BASED THEREON

(71) Applicant: SUMITOMO CHEMICAL COMPANY, LIMITED, Tokyo (JP)

(72) Inventors: Scott Gaynor, Midland, MI (US); Michael Inbasekaran, Palatine, IL (US); James J. O'Brien, Midland, MI (US); Dean M. Welsh, Midland, MI (US)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/683,575

(22) Filed: Nov. 21, 2012

(65) Prior Publication Data

US 2013/0085258 A1 Apr. 4, 2013

Related U.S. Application Data

(62) Division of application No. 10/579,341, filed as application No. PCT/US2004/035221 on Oct. 25, 2004, now abandoned.

(60) Provisional application No. 60/520,596, filed on Nov. 17, 2003.

(51) Int. Cl.
*C07C 211/00* (2006.01)
*C08G 73/02* (2006.01)
(Continued)

(52) U.S. Cl.
CPC .............. *C08G 73/02* (2013.01); *C07C 211/60* (2013.01); *C07C 211/61* (2013.01); *C07D 209/86* (2013.01); *C07D 241/46* (2013.01); *C07D 265/38* (2013.01); *C07D 279/18* (2013.01); *H01L 51/0035* (2013.01); *H01L 51/0039* (2013.01); *H01L 51/0043* (2013.01); *H01L 51/5048* (2013.01); *C07C 2102/06* (2013.01);
(Continued)

(58) Field of Classification Search
CPC ....................................................... C08G 73/02
See application file for complete search history.

(56) References Cited

U.S. PATENT DOCUMENTS 4,983,482 A 1/1991 Ong et al.
5,728,801 A 3/1998 Wu et al.
(Continued)

FOREIGN PATENT DOCUMENTS

CN 1263542 A 8/2000
CN 1273646 A 11/2000
(Continued)

OTHER PUBLICATIONS

Korean Office Action for Korean Patent Application No. 10-2006-7009469, dated Apr. 21, 2011.
(Continued)

*Primary Examiner* — Clinton Brooks
(74) *Attorney, Agent, or Firm* — Sughrue Mion, PLLC

(57) ABSTRACT

Crosslinkable arylamine compounds, oligomers and polymers prepared from such crosslinkable arylamine compounds, films and coatings, and multilayer electronic devices comprising such films are disclosed.

10 Claims, 3 Drawing Sheets

● No interlayer
○ Uncrosslinked interlayer
■ Crosslinked interlayer

(51) Int. Cl.
| | |
|---|---|
| C07C 211/60 | (2006.01) |
| C07C 211/61 | (2006.01) |
| C07D 209/86 | (2006.01) |
| C07D 241/46 | (2006.01) |
| C07D 265/38 | (2006.01) |
| C07D 279/18 | (2006.01) |
| H01L 51/00 | (2006.01) |
| H01L 51/50 | (2006.01) |

(52) U.S. Cl.
CPC ........... C07C 2103/18 (2013.01); Y02E 10/549 (2013.01)

(56) References Cited

U.S. PATENT DOCUMENTS

| | | | |
|---|---|---|---|
| 5,777,070 | A | 7/1998 | Inbasekaran et al. |
| 5,929,176 | A | 7/1999 | Kim et al. |
| 5,929,194 | A | 7/1999 | Woo et al. |
| 5,962,631 | A | 10/1999 | Woo et al. |
| 6,107,452 | A | 8/2000 | Miller et al. |
| 6,169,163 | B1 | 1/2001 | Woo et al. |
| 6,232,376 | B1 | 5/2001 | Tsukada et al. |
| 6,255,447 | B1 | 7/2001 | Woo et al. |
| 6,255,449 | B1 | 7/2001 | Woo et al. |
| 6,277,750 | B1 | 8/2001 | Pawlowski et al. |
| 6,287,713 | B1 | 9/2001 | Heuer et al. |
| 6,309,763 | B1 | 10/2001 | Woo et al. |
| 6,362,310 | B1 | 3/2002 | Woo et al. |
| 6,512,083 | B1 | 1/2003 | Woo et al. |
| 6,514,632 | B1 | 2/2003 | Woo et al. |
| 6,559,256 | B2 | 5/2003 | Holmes et al. |
| 6,605,373 | B2 | 8/2003 | Woo et al. |
| 7,893,160 | B2 * | 2/2011 | Inbasekaran ............ C07C 25/22 257/40 |
| 2004/0054152 | A1 | 3/2004 | Meerholz et al. |
| 2007/0096082 | A1 | 5/2007 | Gaynor et al. |
| 2007/0102695 | A1 | 5/2007 | Inbasekaran et al. |
| 2007/0126345 | A1 | 6/2007 | Hudack et al. |

FOREIGN PATENT DOCUMENTS

| | | | |
|---|---|---|---|
| JP | 10025458 | A | 1/1998 |
| JP | 2000026836 | A | 1/2000 |
| JP | 2001011429 | A | 1/2001 |
| JP | 2001040310 | A | 2/2001 |
| JP | 2003034715 | A | 2/2003 |
| JP | 2003147347 | A | 5/2003 |
| JP | 2007511636 | A | 5/2007 |
| JP | 2007528916 | A | 10/2007 |
| TW | 419929 | B | 1/2001 |
| WO | 9954385 | A1 | 10/1999 |
| WO | 2004060970 | A1 | 7/2004 |
| WO | 2004072123 | A2 | 8/2004 |

OTHER PUBLICATIONS

Korean Office Action for Korean Patent Application No. 10-2011-7025008, dated Jan. 10, 2012.
Korean Office Action dated Apr. 2, 2012 issued in corresponding Korean Patent Application No. 10-2006-7009469.
Korean Intellectual Property Office, "Notice of Preliminary Rejection," issued in connection with Korean Patent Application No. 10-2012-7020085, dated Oct. 9, 2012.
Japanese Patent Office, "Office Action," issued in connection with Japanese Patent Application No. 2011-157891, dated Oct. 26, 2012.
Cha Ki-Hyuk; Jin, Myung-Jong, Dep. Chem. Eng., Inha Univ., Inchon 402-751, S. Korea Konop Hwahak (1994), 5(3), 438-42 published by Korean Society of Industrial and Engineering Chemistry.
Chen et al., J. Org. Chem. 1961, 26, 2721-2727.
Norio Miyaura et al., "Palladium-Catalyzed Cross-Coupling Reactions of Organoboron Compounds", Chemical Review, 1995, pp. 2457-2483, vol. 95, American Chemical Society.

I. Colon et al., "High Molecular Weight Aromatic Polymers by Nickel Coupling of Aryl Polychlorides", Journal of Polymer Science: Part A: Polymer Chemistry Edition, 1990, pp. 367-383, vol. 28, John Wiley & Sons, Inc.
Ismael Colon et al., "Coupling of Aryl Chlorides by Nickel and Reducing Metals", Journal of Organic Chemistry, 1986, pp. 2627-2637, vol. 51, American Chemical Society.
Masahiko Iyoda et al., "Homocoupling of Aryl Halides Using Nickel(II) Complex and Zinc in the Presence of Et₄NI. An Efficient Method for the Synthesis of Biaryls and Bipyridines", Bulletin of the Chemical Society of Japan, 1990, pp. 80-87, vol. 63, No. 1, The Chemical Society of Japan.
Takakazu Yamamoto, "Electrically Conducting and Thermally Stable n-Conjugated Poly(Arylene)S Prepared by Organometallic Processes", Progress in Polymer Science, 1992, pp. 1153-1205, vol. 17, Pergamon Press Ltd.
Wayne R. Sorenson et al., "Preparative Methods of Polymer Chemistry", Second Edition, 1968, pp. 1-504, Interscience Publishers.
P.E. Burrows et al., "Metal ion dependent luminescence effects in metal tris-quinolate organic heterjunction light emitting devices", Applied Physics Letters, 1994, pp. 2718-2720, vol. 64, No. 20, American Institute of Physics.
Yuji Hamada et al., "High Luminance in Organic Electroluminescent Devices with Bis(10-hydroxybenzo[h]quinolinato)beryllium as an Emitter", Chemistry Letters, 1993, pp. 905-906, The Chemical Society of Japan.
Yuji Hamada et al., "Organic Electroluminescent Devices with Bright Blue Emission", Optoelectronics-Devices and Technologies, 1992, pp. 83-93, vol. 7, No. 1, MITA Press.
Junji Kido et al., "Blue Electroluminescent 1,2,4-Triazole Derivative", Chemistry Letters, 1996, pp. 47-48.
Masayoshi Yoshida et al., "Three-layered multicolor organic electroluminescent device", Applied Physics Letters, 1996, pp. 734-736, vol. 69, No. 6, American Institute of Physics.
Xiao-Chang Li et al., "Synthesis and Optoelectronic Properties of Aromatic Oxadiazole Polymers", Journal of Chemical Society, Chemical Commun., 1995, pp. 2211-2212.
Y. Yang et al., "Electron injection polymer for polymer light-emitting diodes", Journal of Applied Physics, 1995, pp. 4807-4809, vol. 77, No. 9, American Institute of Physics.
Marko Strukelj et al., "Design and Application of Electron-Transporting Organic Materials", Science, 1995, pp. 1969-1972, vol. 267.
Takakazu Yamamoto et al., "Polymer Light-Emitting Diodes with Single- and Double-Layer Structures Using Poly(2,3-diphenylquinoxaline-5,8-diyl)", Japan Jounral of Applied Physics, 1994, pp. L250-L253, vol. 33, Part 2, No. 2B.
D. O'Brien et al., "Electroluminescence applications of a poly(phenyl quinoxaline)", Synthetic Metals, 1996, pp. 105-108, vol. 76, Elsevier Science S.A.
M.S. Weaver et al., "Recent progress in polymers for electroluminescence: microcavity devices and electron transport polymers", Thin Solid Films, 1996, pp. 39-47, vol. 273, Elsevier Science S.A.
M.S. Bayerl: "Crosslikable hole-transport materials for preparation of multilayer organic light emitting devices by spin-coating", Macromolecular: Rapid Communcations, Wiley VCH, Weinheim, DE, vol. 20, No. 4, 1999, (XP002193426), pp. 224-228.
T. Braig: "Crosslinkable hole-transporting polymers by palladium catalyzed C-N-coupling reaction", Macromolecular: Rapid Communications, Wiley VCH, Weinheim, DE, vol. 21, No. 9, Jun. 2000, (XP002193425), pp. 583-589.
Korean Intellectual Property Office, "Notice of Final Rejection," issued in connection with Korean Patent Application No. 10-2011-7025008, dated Nov. 30, 2012 English language Translation.
German Patent Office, "Official Action," issued in connection with German Patent Application No. 11 2004 002 204.5, dated Jun. 6, 2014 English language Translation.
Office Action issued in Chinese Patent Application No. 201210261895.5 dated Nov. 27, 2013.
G. Klarner, et al. "Cross-linkable Polymers Based on Dialkylfluorenes", Chem. Mater. 1999, 11, pp. 1800-1805.

* cited by examiner

US 9,399,702 B2

CROSSLINKABLE ARYLAMINE COMPOUNDS AND CONJUGATED OLIGOMERS OR POLYMERS BASED THEREON

CROSS-REFERENCE TO RELATED APPLICATIONS

This application is a divisional of U.S. patent application Ser. No. 10/579,341, filed Aug. 24, 2006, which is a National Phase Application of PCT/US2004/035221, filed Oct. 25, 2004, and claims benefit to U.S. Provisional Patent Application No. 60/520,596, filed Nov. 17, 2003. The contents of U.S. patent application Ser. No. 10/579,341 are incorporated herein by reference in its entirety.

BACKGROUND OF THE INVENTION

This invention relates to novel crosslinkable arylamine compounds and methods for their preparation. The invention further relates to oligomers and polymers of such compounds, including crosslinked derivatives thereof, as well as films and coatings prepared from such compounds, oligomers or polymers, processes for preparing such films and coatings, and electronic devices, especially electroluminescent devices, comprised of one or more layers of such polymer films.

U.S. Pat. Nos. 6,605,373, 6,362,310, 6,255,449, 6,255,447, 6,169,163, 5,962,631 and related patents disclosed certain crosslinkable substituted fluorene compounds and oligomers and polymers therefrom. U.S. Pat. No. 5,929,194 disclosed the synthesis of polyarylpolyamines by crosslinking of certain small molecule amines containing two reactive groups. Related disclosures are also found in U.S. Pat. No. 5,728,801.

*Macromolecular Rapid Communication* 21, 583-589 (2000) described the synthesis of arylamine containing crosslinkable hole transport materials containing a crosslinkable oxetane group. *Macromolecular Rapid Communication* 20, 224-228 (1999) described the synthesis of triarylamine small molecules with crosslinkable oxetane groups that can be spin-coated and crosslinked as films. The foregoing references, to the extent crosslinked polymers are disclosed, lack a conjugated polymer backbone, and have only restricted charge transport ability.

Recent advances in photodisplay technology have resulted in improved compounds and fabrication techniques for electroluminescent devices such as light-emitting diodes (LED's). High luminosity materials are now available for a large portion of the visible light spectrum, including blue light emitting compounds. Recently it has been discovered that improved lifetimes and efficiencies of the active or light emitting layer of a multilayer LED can be obtained by incorporation of a charge transport layer into a multilayer LED between the active or light emitting layer and the anode. Such layers may also be referred to as a hole injection and/or hole transport layer where the purpose is to improve hole injection into the light emitting layer and to provide a buffer layer between the anode and the light emitting layer. In other applications, such an inter layer between the hole transport layer and light emitting layer has been shown to provide improved device efficiency and lifetime.

The present invention is directed to novel compounds for use in various layers of a multilayer LED, such as hole transport layers and interlayers of a multilayer LED, as well as in other electronic devices such as field effect transistors (FET's), photovoltaic cells, and even for integrated circuits or printed circuit boards.

SUMMARY OF THE INVENTION

In one aspect, this invention is an arylamine compound of the formula:

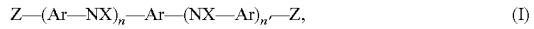
$$Z—(Ar—NX)_n—Ar—(NX—Ar)_{n'}—Z, \quad (I)$$

wherein,

Ar independently each occurrence is a group comprising one or more divalent aromatic groups, and optionally two Ar groups separated by a single NX group may be joined together by a second covalent bond or by a bridging group, thereby forming a fused multiple ring system;

X is an inert substituent or a cross-linkable group, with the proviso that in at least one occurrence in said compound, X is a crosslinkable group;

Z independently each occurrence is hydrogen or a leaving group, n is 1 or 2; and n' is 0, 1 or 2.

Due to the pendant nature of the crosslinkable group, X, the compounds of the present invention are capable of forming oligomers and polymers containing relatively large amounts of conjugated unsaturation, thereby resulting in improved charge transport properties. Oligomers and polymers, including copolymers, resulting from crosslinking compositions comprising the foregoing compounds advantageously are characterized by reduced ionization potential and improved conductivity. Moreover, the compounds are capable of forming crosslinked, solvent resistant films that are well suited for use as interlayers in electroluminescent devices.

Accordingly, in a second aspect, this invention is a composition comprising oligomers, polymers, or crosslinked derivatives thereof having one or more repeating groups of the formula:

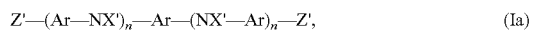
$$Z'—(Ar—NX')_n—Ar—(NX'—Ar)_{n'}—Z', \quad (Ia)$$

where X' is X or a divalent crosslinked remnant formed by addition polymerization of a crosslinkable X group, preferably such a group that forms conjugated unsaturation upon crosslinking;

Z' is Z, a covalent bond, or a terminal group formed by replacement or reaction of a leaving group; and Ar, X, Z, n and n' are as previously defined with respect to compounds of formula (I).

In a third aspect, this invention is a process for preparing oligomers, polymers, including copolymers, and crosslinked derivatives thereof comprising one or more groups of formula (Ia), which process comprises heating one or more compounds of formula (I) or a composition comprising the same, such as a mixture thereof with one or more addition polymerizable monomers, optionally in the presence of any other noninterfering compound, under reaction conditions sufficient to form an oligomer or polymer having one or more repeating groups of Formula (Ia).

In a fourth aspect, this invention is a film comprising one or more of the oligomers or polymers of the second embodiment of this invention or preparable according to the third embodiment of this invention.

In a fifth aspect, this invention is an electroluminiscent device comprising one or more layers of polymer films, at least one of which comprises a film according to the fourth aspect of the invention.

The foregoing compounds, oligomers and polymers have been discovered to possess especially efficient hole injecting/ transporting or electron blocking properties when used to form interlayers in electronic devices, and advantageously are characterized by reduced ionization potential and improved conductivity. Moreover, the compounds are capable of forming crosslinked, solvent resistant films that are well suited for use as such interlayers in electronic devices such as LEDs.

DETAILED DESCRIPTION OF THE INVENTION

Figure 1:
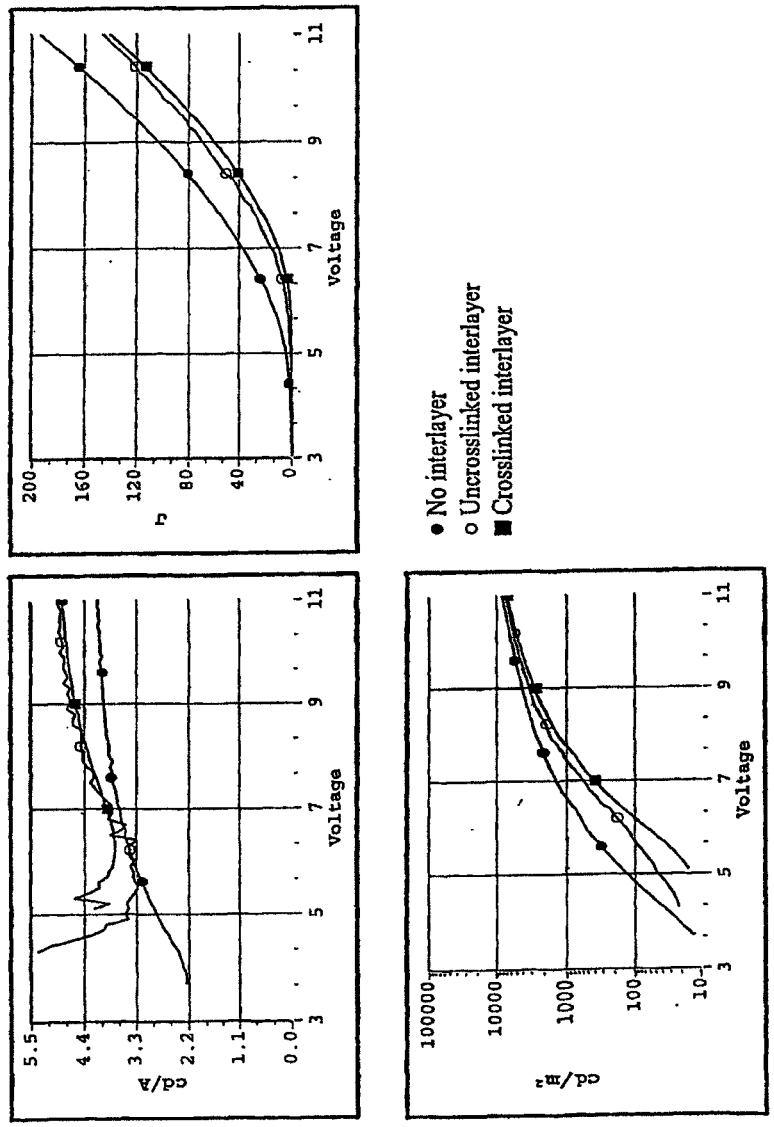
FIG. 1 contains electrical properties of the light emitting devices of Example 6.

For purposes of United States patent practice, the contents of any patent, patent application or publication referenced herein is hereby incorporated by reference in its entirety herein, especially with respect to its disclosure of monomer, oligomer or polymer structures, synthetic techniques and general knowledge in the art. If appearing herein, the term "comprising" and derivatives thereof is not intended to exclude the presence of any additional component, step or procedure, whether or not the same is disclosed herein. In order to avoid any doubt, all compositions claimed herein through use of the term "comprising" may include any additional additive, adjuvant, or compound, unless stated to the contrary. In contrast, the term, "consisting essentially of" if appearing herein, excludes from the scope of any succeeding recitation any other component, step or procedure, excepting those that are not essential to operability. The term "consisting of", if used, excludes any component, step or procedure not specifically delineated or listed. The term "or", unless stated otherwise or apparent from the context, refers to the listed members individually as well as in any combination.

As used herein the term "aromatic" refers to a polyatomic, cyclic, ring system containing $(4\delta+2)$ π-electrons, wherein $\delta$ is an integer greater than or equal to 1. The term "fused" as used herein with respect to a ring system containing two or more polyatomic, cyclic rings means that with respect to at least two rings thereof, at least one pair of adjacent atoms is included in both rings.

"B-Staged" refers to the oligomeric mixture or low molecular weight polymeric mixture resulting from partial polymerization of a monomer. Unreacted monomer may be included in the mixture.

"Conjugation" refers to full or partial overlap of adjacent π-, p- or d-orbital electrons associated with atoms in the polymer chain of interest. Conjugation is presumed to exist between two entities containing atoms possessing delocalized charges, such as double or triple bonds, which are joined to one another by a covalent bond or by a —S—, —O—, —NR—, —PR—, BR—, or —SiR$_2$— group.

"Crosslinkable" means a functional group that is capable of being irreversibly cured or polymerized, thereby forming a material that cannot be reshaped or reformed. Crosslinking may be assisted by heat or by UV, microwave, x-ray, or e-beam irradiation. The term is often used interchangeably with "thermosettable" when the crosslinking is done thermally.

"Hydrocarbyl" refers to a univalent moiety containing only carbon and hydrogen atoms.

"Hydrocarbylene" refers to a divalent moiety containing only carbon and hydrogen atoms.

"Inert substituent" means a substituent group which does not interfere with any subsequent desirable coupling or polymerization reaction of the monomer or oligomer but may include further polymerizable moieties as disclosed herein. Suitable inert non-polymerizable substituents include hydrogen, $C_{1-20}$ hydrocarbyl and tri($C_{1-20}$hydrocarbyl)silyl groups.

"Leaving group" means a substituent that is readily displaced or eliminated from the molecule under coupling conditions. Examples of suitable leaving groups include halo, cyano, triflate, azide, —B(OR$^1$)$_2$, and

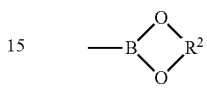

wherein R$^1$, independently in each occurrence, is hydrogen or a $C_{1-10}$ alkyl group, and R$^2$, independently each occurrence, is a $C_{2-10}$ alkylene group. A preferred leaving group is bromo.

Examples of crosslinkable X groups are moieties containing a double bond, a triple bond, a precursor capable of in situ formation of a double bond, or a heterocyclic, addition polymerizable group. Preferred crosslinkable X groups include benzocyclobutanyl groups and substituted $C_{6-12}$ arylene groups containing one or more substituents selected from the group consisting of benzocyclobutane, azide, oxirane, di(hydrocarbyl)amino, cyanate ester, hydroxy, glycidyl ether, $C_{1-10}$ alkylacrylate, $C_{1-10}$ alkylmethacrylate, ethenyl, ethenyloxy, perfluoroethenyloxy, ethynyl, maleimide, nadimide, tri($C_{1-4}$)-alkylsiloxy, tri($C_{1-4}$)alkylsilyl, and halogenated derivatives thereof. Most preferred crosslinkable X groups are 1-benzo-3,4-cyclobutane and 4-phenyl-1-(benzo-3,4-cyclobutane).

Specific examples of suitable crosslinkable X groups include:

—(R$^4$)$_p$—CR$^3$=CR$^3$$_2$,   —(R$^4$)$_p$—C≡CR$^3$,   —(R$^4$)$_p$—O(R$^4$)$_p$ CR$^3$=CR$^3$$_2$, —(R$^4$)$_p$—O(R$^4$)$_p$ C≡CR$^3$,

—(R$^4$)$_p$—CO(R$^4$)$_p$   CR$^3$=CR$^3$$_2$,   —(R$^4$)$_p$—CO(R$^4$)$_p$ C≡CR$^3$, —(R$^4$)$_p$—OC(R$^4$)$_p$ CR$^3$=CR$^3$$_2$,

—(R$^4$)$_p$—OC(R$^4$)$_p$   C≡CR$^3$,   —(R$^4$)$_p$—OCO(R$^4$)$_p$ CR$^3$=CR$^3$$_2$, —(R$^4$)$_p$—OCO(R$^4$)$_p$ C≡CR$^3$,

—(R$^4$)$_p$—O(CO)O(R$^4$)$_p$ CR$^3$=CR$^3$$_2$, —(R$^4$)$_p$—O(CO)O (R$^4$)$_p$—C≡CR$^3$, NR$^3$$_2$,

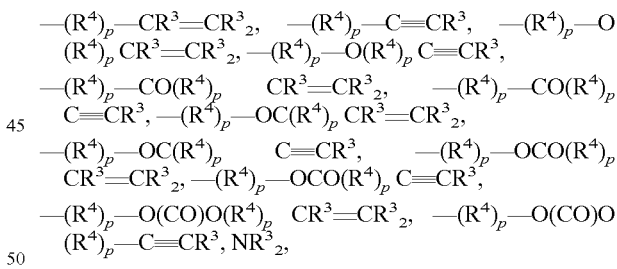

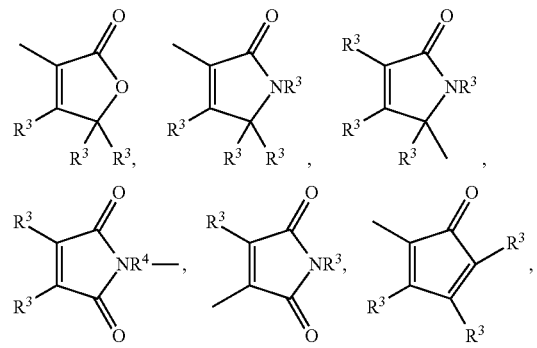

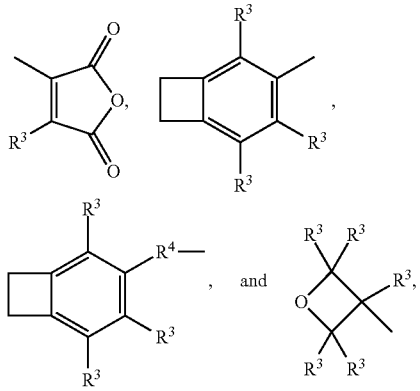

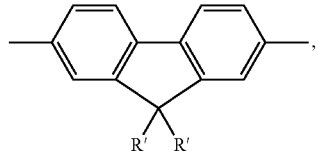

where R', independently each occurrence, is an inert substituent, X or X'.

As previously mentioned, two Ar groups separated by a single —NX— group may form a fused aromatic ring system. Examples include groups corresponding to the formulas:

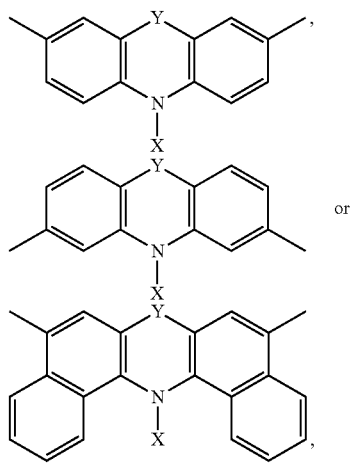

where, X is as previously defined;

Y is a covalent bond, O, S or NR; where

R independently in each occurrence is i) hydrogen; ii) halogen; iii) a $C_{1-20}$ hydrocarbyl group; iv) a hydrocarbyl group substituted with one or more heteroatom containing groups containing up to 20 atoms not counting hydrogen and wherein the heteroatom is selected from S, N, O, P, B or Si; v) a halogenated derivative of iii) or iv); or vi) a substituted derivative of iii) or iv) wherein the substituent is a crosslinkable X group.

Preferred substituents, R, include $C_{1-40}$ hydrocarbyl groups or $C_{1-40}$ hydrocarbyl groups containing one or more S, N, O, P, or Si heteroatoms, and the foregoing $C_{1-40}$ hydrocarbyl or $C_{1-40}$ heteroatom containing groups substituted by a crosslinkable X group. In a more preferred embodiment, R is a $C_{1-10}$ alkyl group.

The monomers, oligomers and polymers of the invention preferably are highly conjugated, if not completely conjugated, along the backbone defined by —(Ar—NX')$_n$—Ar—(NX'—Ar)$_n'$—. In a further preferred embodiment, they comprise difunctional derivatives of both fluorene and triarylamines in this backbone. More preferably still, the crosslinked oligomers and polymers of the invention are also highly conjugated, if not completely conjugated, along the crosslinked structure defined by at least one:

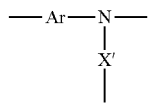

where $R^3$ is hydrogen, halogen, $C_{1-20}$ hydrocarbyl, $C_{1-20}$ halohydrocarbyl, or $C_{1-20}$ halocarbyl;

$R^4$ is $C_{1-20}$ hydrocarbylene, $C_{1-20}$ halohydrocarbylene, or $C_{1-20}$ halocarbylene; and p is 0 or 1.

In like vein, X' is either X or a crosslinked remnant of X. It will be understood by the skilled artisan, that crosslinking of an X functional group involves a reaction between two or more X groups in two or more different compounds, oligomers or polymers, or a reaction of an X group with a separately added polymerizable comonomer, thereby joining said molecules into a single chemical entity.

In one preferred embodiment of the invention, X groups comprise an aromatic moiety, preferably a moiety of the formula ArX", wherein Ar is as previously defined and X" is a crosslinkable group having at least one of the crosslink forming atoms thereof covalently bound to an atom of Ar bearing delocalized electronic charge. That is, the X" group is directly attached to an aromatic group comprising Ar. Especially suited X" groups in this embodiment include 1-ethenyl or benzo-3,4-cyclobutan-1-yl groups, and inertly substituted derivatives thereof. In yet another preferred embodiment, the X" groups are self-crosslinkable, meaning that no initiator, such as an acid, base or peroxide compound, is needed to initiate crosslinking involving said X" group, it being understood that copolymerizable comonomers, especially addition polymerizable comonomers such as ethylenically unsaturated compounds, may additionally be present. In this embodiment, the absence of an acid, base or peroxide initiator, reduces corrosion of the cathode or other components of the resulting electronic device and eliminates problems due to proton migration within the interlayer.

Suitable inert, non-crosslinkable, X groups include $C_{1-20}$ hydrocarbyl and halogenated $C_{1-20}$ hydrocarbyl groups, especially aryl and alkaryl groups. Preferred non-crosslinkable X groups include phenyl and $C_{1-10}$ alkylphenyl, especially p-n-butylphenyl.

Suitable Ar groups include phenylene, biphenylene, naphthalenediyl, anthracenediyl, stilbenediyl, and fluorenediyl groups, inertly substituted derivatives thereof, and combinations of the foregoing groups. Preferred fluorenediyl groups correspond to the formula:

group.

Highly preferred embodiments of the foregoing compounds are those wherein Ar each occurrence is 1,4-phenylene, 9,9-di($C_{1-20}$alkyl)fluoren-2,7-diyl, or a combination thereof; X is 3,4-benzocyclobutan-1-yl, ethenyl or p-ethenylphenyl; Z is bromine or hydrogen; n is 1 or 2; and n' is 0 or 1. Further preferred amongst these compounds are those wherein Ar each occurrence is phenylene; each X group is 3,4-benzocyclobutan-1-yl; Z each occurrence is bromine; n is 1 or 2; and n' is 0. Highly preferably, within the forgoing compounds n is 1.

Specific examples of the compounds of formula I) according to the present invention are those having the following structures:

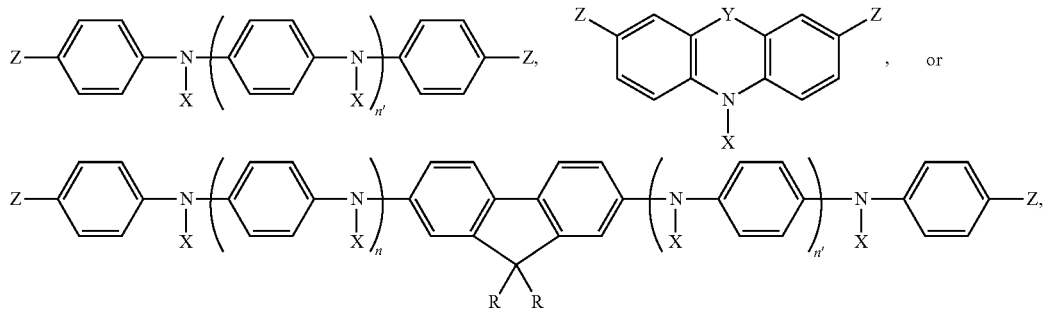

where n, n', R, X, Y and Z are as previously defined.

Specific examples of the oligomers and polymers of formula Ia) according to the present invention are those having the following structures:

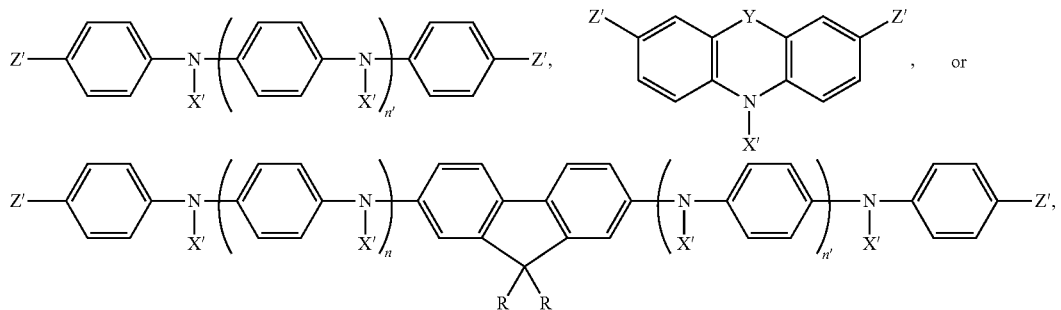

where n, n', R, X', Y and Z' are as previously defined. Such oligomers and polymers are readily prepared using conventional synthetic techniques to cause loss or polymerization of the leaving group, Z, and formation of the remnant, Z'. Suitable techniques include the well known Buchwald or half-Buchwald reaction, Suzuki coupling reactions, or similar techniques.

The oligomers and polymers are highly suited for use in the preparation of both hole transport films and interlayer films in electroluminiscent devices.

Crosslinking of Monomers

The arylamine compounds of formula I) or Ia) of the invention are readily polymerized to form crosslinked oligomers or polymers by heating a composition comprising such compound at an elevated temperature for a time sufficient to result in addition polymerization or other crosslinking reaction of at least some X functionality. In one embodiment the compounds are copolymerized with one or more copolymerizable monomers capable of forming divalent crosslinking moieties.

Preferred copolymerizable compounds for use herein correspond to the formulas (II) or (III):

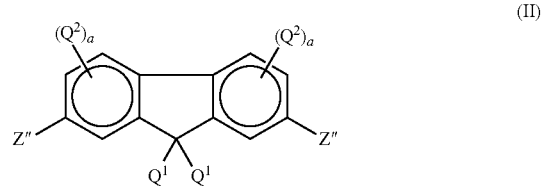

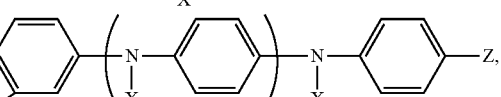

wherein $Q^1$ is independently in each occurrence $C_{1-20}$ hydrocarbyl or $C_{1-20}$ hydrocarbyl containing one or more S, N, O, P or Si atoms, $C_{4-16}$ hydrocarbyl carbonyloxy, $C_{4-16}$ aryl(trialkylsiloxy) or both $Q^1$ may form with the 9-carbon on the fluorene ring a $C_{5-20}$ ring structure or a $C_{4-20}$ ring structure containing one or more of S, N or O;

$Q^2$ is independently in each occurrence $C_{1-20}$ hydrocarbyl, $C_{1-20}$ hydrocarbyloxy, $C_{1-20}$ thioether, $C_{1-20}$ hydrocarbylcarbonyloxy or cyano;

$Q^3$ is independently in each occurrence $C_{1-20}$ hydrocarbyl or $C_{1-20}$ hydrocarbyl substituted with di($C_{1-20}$alkyl)amino, $C_{1-20}$ hydrocarbyloxy or $C_{1-20}$ hydrocarbyl or tri($C_{1-10}$ alkyl) siloxy;

a is independently in each occurrence 0 or 1; and

Z" is a leaving group, especially bromo.

In a preferred embodiment, the oligomers and polymers of the invention comprise from 1 to 99 percent, more preferably from 2 to 50 percent, and most preferably from 2 to 10 percent of repeat units of formula Ia) and 99 to 1 percent, more preferably 98 to 50 percent, most preferably 98 to 90 percent of repeat units of the formula:

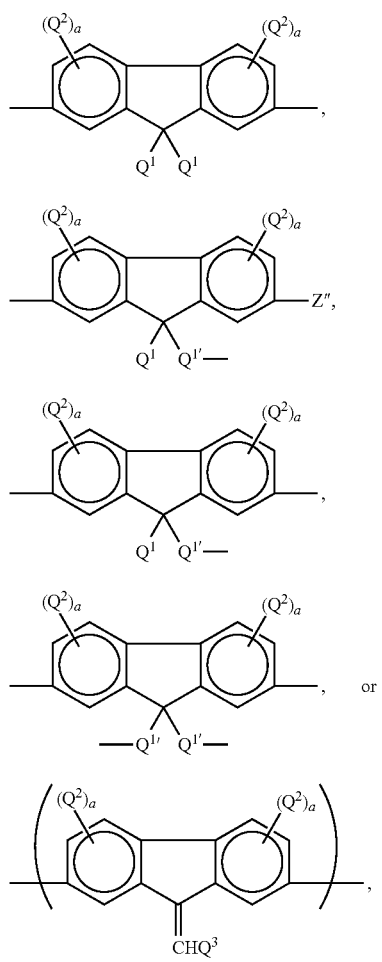

wherein $Q^{1'}$ is a covalent bond or the divalent remnant of $Q^1$.

The monomers and oligomers or b-staged derivatives of the invention are readily soluble in common organic solvents. They are processible into thin films or coatings by conventional techniques, particularly solution spin coating or ink-jet printing, with or without the use of a solvent.

The oligomers or polymers of this invention preferably have a weight average molecular weight of 1000 Daltons or greater, more preferably 5000 Daltons or greater, even more preferably 10,000 Daltons or greater, highly preferably 15,000 Daltons or greater and most preferably 20,000 Daltons or greater; preferably 1,000,000 Daltons or less, more preferably 500,000 Daltons or less and most preferably 200,000 Daltons or less. Molecular weights are determined by use of gel permeation chromatography using polystyrene standards. The degree of polymerization of the polymers of the invention as measured by the number of repeat units therein is preferably at least 2, more preferably at least 3. Preferably, the oligomers or polymers demonstrate a polydispersity (Mw/Mn) of 5.0 or less, more preferably 3.0 or less, and most preferably 2.0 or less.

Processes for Preparing Oliomers or Polymers

The compounds, oligomers and polymers of the invention are prepared by any suitable process, including a condensation reaction of an aromatic boronate and a bromide, commonly referred to as the "Suzuki reaction", as reported by N. Miyaua and A. Suzuki in *Chemical Reviews*, Vol. 95, pp. 457-2483 (1995). This palladium catalyzed reaction can be applied to preparing high molecular weight polymers and copolymers with addition of a phase transfer catalyst as taught in U.S. Pat. No. 5,777,070. The reaction is typically conducted from 70° C. to 120° C. in suitable solvent or diluent. Preferred solvents include aromatic hydrocarbons, such as toluene or diethylbenzene, or aliphatic or aromatic ethers, esters, or carbamates, such as tetrahydrofuran or dimethylformamide. Mixtures of the foregoing solvents or diluents may be employed as well. A most preferred solvent is toluene. An aqueous base, preferably sodium carbonate or bicarbonate, is used as a scavenger for the reaction product of the leaving group, generally HBr. Depending on the reactivities of the reagents and the molecular weight of the desired product, a polymerization reaction may take from 1 minute to 100 hours. A monofunctional aryl halide or an aryl boronate compound may be added as a chain-terminator in such reactions, thereby resulting in the formation of a terminal aryl group.

Polymerization processes involving only dihalo-functional reactants used in the formation of compounds according to the present invention may also be carried out using nickel catalyzed coupling reactions. One such coupling reaction was described by Colon et al. in *Journal of Polymer Science*, Part A, Polymer Chemistry Edition, Vol. 28, p. 367 (1990), incorporated herein by reference, and by Colon et al. in *Journal of Organic Chemistry*, Vol. 51, p. 2627 (1986). The reaction is typically conducted in a polar aprotic solvent (e.g., dimethylacetamide) with a catalytic amount of nickel salt, a substantial amount of triphenylphosphine and a large excess of zinc dust. A variant of this process is described by Ioyda et al. in *Bulletin of the Chemical Society of Japan*, Vol. 63, p. 80 (1990) wherein an organo-soluble iodide was used as an accelerator. Another nickel-catalyzed coupling reaction was disclosed by Yamamoto in *Progress in Polymer Science*, Vol. 17, p. 1153 (1992) wherein a mixture of dihaloaromatic compounds were treated with an excess amount of nickel (1,5-cyclooctadiene) complex in an inert solvent. All nickel-catalyzed coupling reactions when applied to reactant mixtures of two or more aromatic dihalides yield essentially random copolymers. Such polymerization reactions may be terminated by the addition of small amounts of water to the polymerization reaction mixture, thereby replacing the terminal halogen groups with hydrogen groups. Alternatively, a monofunctional aryl halide may be used as a chain-terminator, resulting in the formation of a terminal aryl group.

Copolymers Containing Other Conjugated Groups

The polymers of the invention desirably contain conjugated unsaturated groups. "Conjugated groups" refers to moieties containing two or more double bonds, triple bonds and/or aromatic rings, separated by a single covalent bond. The incorporation of such groups into the polymer may be used to modify the light absorption, ionization potential, and/or electronic properties of the polymer. Preferred unsaturated groups present in the conjugated unsaturated group containing comonomers for use herein include divalent derivatives of hydrocarbons such as divalent derivatives of benzene, naphthalene, acenaphthene, phenanthrene, anthracene, fluoranthene, pyrene, rubrene, and chrysene, as well as unsaturated heterocyclic groups, such as divalent derivatives of furan, thiophene, pyrrole, oxazole, isooxazole, thiazole, isothiazole, imidazole, oxadiazoles, thiadiazole, pyrazole, pyridine, pyridazine, pyrimidine, pyrazine, triazine, tetrazene; benzoxazole, benzothiazole, bennimidazole, quinoline, isoquinoline, cinnoline, quinazoline, quinoxaline, phthalazine, benzothiadiazole, benzotriazine, phenazine, phenanthridine, acridine, carbazole, and diphenylene oxide. Highly desirable copolymerizable conjugated unsaturated groups include 9,9-disubstituted fluorenediyl groups and triarylamine groups.

It is possible to control the sequencing of the monomeric units in the resulting copolymers by controlling the order and composition of monomer feeds, especially when employing a Suzuki reaction. For instance, a high molecular weight copolymer comprising mainly large blocks of polyfluorenediyl homopolymers connected to short blocks of alternating diarylamine-comonomer oligomers may be made by first introducing into the reaction suitable reactants in the appropriate ratio to make the alternating fluorenediyl-comonomer oligomers followed by the remainder of diarylamine monomers so long as there is an overall stoichiometric balance of the reagents, that is, the boron and bromine containing reagents.

Examples of diarylamine groups that may be additionally incorporated into the copolymers of the invention are tertiary aromatic amines containing two reactive substituents. Such compounds result in the inclusion of the corresponding triarylamine remnant into the copolymer. Examples of suitable tertiary aromatic amines include, triphenyl amine, alkyldiaryl amines, N,N,N',N'-tetraphenylbenzidine, and N,N,N',N'-tetraphenyl-1,4-phenylenediamine.

In general, copolymerizable, conjugated compounds containing up to 60 carbons are useful for the present purpose. They may be substituted optionally with one or more substituents that are not deleterious to the photoluminescent properties of the polymer compositions. Examples of suitable substituents include $C_1$-$C_{20}$ hydrocarbyl radicals, $C_1$-$C_{20}$ (thio)alkoxy radicals, $C_1$-$C_{20}$ (thio)aryloxy radicals, cyano, fluoro, chloro, $C_1$-$C_{20}$ alkoxycarbonyl, $C_1$-$C_{20}$ aryoxylcarbonyl, $C_1$-$C_{20}$ carboxyl and alkyl(aryl)sulfonyl radicals. Substituents which are known photoluminescent quenchers, such as arylcarbonyl and nitro groups, are undesirable and should be avoided.

Polymer Blends

The oligomers and polymers of invention may be used in forming a blend of at least two polymers. If desired, one or more of the oligomers or polymers of the blend may be a light-emitting polymer. Suitably the blend is composed of one or more polymeric materials selected from polystyrene, polybutadiene, poly(methyl methacrylate), poly(ethylene oxide), phenoxy resins, polycarbonates, polyamides, polyesters, polyurethanes, polyimides, crosslinked epoxy resins, crosslinked phenolic resins, crosslinked acrylate resins, and crosslinked urethane resins. Examples of these polymers may be found in *Preparative Methods of Polymer Chemistry*, W. R. Sorenson and T. W. Campbell, Second Edition, Interscience Publishers (1968). Preferably the blends comprising a crosslinked polymer are formed by blending the uncrosslinked components and later crosslinking the components in situ.

Preferably the blend comprises at least two light emitting polymers and the maximum emission wavelength of one of the polymers in the blend is within 25 nm of the maximum absorption wavelength of at least one other polymer in the blend. Highly desirably the blend comprises a mixture of two polymers each corresponding to the present invention in the range from 0.1 to 99.9 and 99.9 to 0.1 percent respectively.

Polymer Applications

The primary use for the oligomers and polymers of the invention is in the formation of films. Such films can be used in preparing photoluminescent or fluorescent coatings as well as interlayers, protective coating, and hole transport layers in electronic devices such as organic light emitting diodes, especially polymeric light-emitting diodes, photovoltaic cells, lighting, photodiodes, sensors, thin film transistors, and other devices. The thickness of the coating or film is dependent upon the ultimate use. Generally, such thickness can be from 0.01 to 200 micrometers. When used as a fluorescent coating, the film thickness is desirably from 50 to 200 micrometers. When used as electronic protective layers, the film thickness is desirably from 5 to 20 micrometers. When used as a layer in a polymeric light-emitting diode, the film thickness is desirably from 0.001 to 2 micrometers. The oligomers or polymers of the invention form films that are substantially lacking in pinholes and other defects. Such films can be prepared by means well known in the art including spin-coating, spray-coating (including ink-jet spraying), dip-coating and roller-coating. Such coatings are prepared by a process wherein a composition comprising the present compounds, oligomers or polymers is applied to a substrate and exposed to conditions such that a film is formed, generally by means of a crosslinking reaction. The conditions which form a film depend upon the application technique and the reactive end groups of the film forming moieties. Preferably, the solution contains from 0.1 to 10 weight percent of the oligomers or polymers of the invention, and the remainder solvent. For thin coatings, it is preferred that the composition contains from 0.5 to 5.0 percent by weight of the compounds, oligomers or polymers. This composition is then applied to the appropriate substrate by the desired method and the solvent is allowed to evaporate. Residual solvent may be removed by vacuum and/or by heat. If the solvent is low boiling, then low solution concentrations, for example, 0.1 to 2 percent, are desired. If the solvent is high boiling, then high concentrations, for example, 3 to 10 percent, are desired. After removal of the solvent, the coating is then exposed to the necessary conditions to cure the film, if needed, thereby preparing a film having high solvent and heat resistance. The films are preferably substantially uniform in thickness and substantially free of pinholes. Preferably, the films are cured when exposed to temperatures of 100° C. or greater, more preferably 150° C. or greater and most preferably 200° C. or greater. Preferably, the films cure at a temperature of 300° C. or less.

In the preparation of the films, the composition may further comprise a catalyst suitable to facilitate or initiate the crosslinking process. Such catalysts are well known in the art, for instance, for materials having ethylenic unsaturation, a free radical catalyst may be used. For aryl moieties with glycidyl ethers as end-groups, ureas or imidazoles may be used. In the preparation of films from fluorenes with glycidyl ether substituted aryl groups as terminal moieties, the materials may be reacted with commonly known curing agents which facilitate crosslinking. Among preferred curing agents are tetrahydrophthalic anhydride, methylbicyclo[2.2.1]heptane-2,3-dicarboxylic anhydride (nadic anhydride), and maleic anhydride.

In another desirable embodiment, the monomers and oligomers may be partially cured or B-staged prior to forming the film. In such embodiment, the composition is exposed to conditions such that a portion of the reactive materials cure and a portion of the reactive materials do not cure. This is commonly used to improve the handleability of composition and can facilitate the preparation of films. Such B-staged material can thereafter be used to prepare coatings by the means disclosed above. Preferably, from 10 to 50 percent of the reactive moieties are reacted during B-staging.

Yet another aspect of the invention relates to organic electroluminescent (EL) devices comprising a film of the polymers of this invention. An organic EL device typically consists of an organic film located between an anode and a cathode in electrical contact therewith, such that when a positive bias is applied to the device, holes are injected into the organic film from the anode, and electrons are injected into the organic film from the cathode. The subsequent combination of a hole with an electron may give rise to an exciton which may undergo radiative decay to the ground state by liberating a photon. In practice the anode is commonly a mixed oxide of indium and tin (ITO), employed for its high conductivity and transparency. The mixed oxide is normally deposited on a transparent substrate such as glass or plastic so that the light emitted by the organic film may be observed. The organic film may be the composite of several individual layers each designed for a distinct function or purpose. Since holes are injected from the anode, the layer next to the anode desirably has suitable functionality for transporting holes. Similarly, the layer next to the cathode desirably has suitable functionality for transporting electrons. In many instances, the hole or electron transporting layer also acts as the emitting layer. In some instances, one layer performs the combined functions of hole transport, electron transport, and light emission. Generally, films comprising the polymers of the present invention act as buffer layers or hole transport layers in an electronic device. In addition to the foregoing polymeric film layers, films of small molecules deposited by thermal evaporation may be incorporated into the electronic device, if desired. It is preferred that the total thickness of the organic film be less than 1000 nm, more preferably less than 500 nm, most preferably less than 300 nm. One embodiment of the instant invention is an EL device in which the organic film comprises at least one of the polymeric compositions of this invention.

The ITO surface which serves as the anode may be coated with a film according to the invention usually after first cleaning the exposed surface with an aqueous detergent solution, an organic solvent, and/or a UV or plasma generated ozone treatment. It may also be coated with a thin layer of a conducting substance to facilitate hole injection if desired. Suitable conducting substances include copper phthalocyanine, polyaniline and poly(3,4-ethylenedioxy-thiophene) (PEDT); the last two of which in their conductive forms are prepared by doping with a strong organic acid, for example, poly (styrenesulfonic acid). It is preferred that the thickness of the conducting layer, when used, be 200 nm or less; more preferably 100 nm or less.

The present compounds may be used in the preparation of interlayers in a multilayer device or as one component of a mixture of compounds forming a hole transporting polymer layer or as a separate hole transporting layer in a multilayer electronic device, especially an electroluminiscent device. In the case where a hole-transporting polymer other than the present invention is used, known hole-conducting polymers, such as polyvinylcarbazole, or the polymeric aryl amines disclosed in U.S. Pat. No. 5,728,801 or 5,929,194 may be employed. The resistance of this layer to erosion by the solution of the copolymer film which is to be applied next is obviously critical to the successful fabrication of multi-layer devices. Accordingly the copolymers of this invention are normally applied from solutions in organic solvents such as xylene or toluene in which the hole-transporting layer is insoluble. By covering or protecting the hole-transporting polymer with an interlayer comprising a crosslinked polymer according to the present invention, the hole-transporting polymer can be protected from subsequent reagents or solvents employed in manufacture of the electronic device. The thickness of the hole-transporting layer or interlayer according to the invention is desirably 500 nm or less, preferably 300 nm or less, most preferably 150 nm or less.

A suitable electron-transporting layer, if used, may be applied either by thermal evaporation of a low molecular weight material or by solution coating of a polymer, such as a polymer according to the present invention, using a solvent that does not significantly damage any previously deposited film layer. Examples of low molecular weight materials conventionally used in forming electron-transporting layers include metal complexes of 8-hydroxyquinoline (as described by Burrows et al. in *Applied Physics Letters*, Vol. 64, pp. 2718-2720 (1994)), metallic complexes of 10-hydroxybenzo(h)quinoline (as described by Hamada et al. in *Chemistry Letters*, pp. 906-906 (1993)), 1,3,4-oxadiazoles (as described by Hamada et al. in *Optoelectronics—Devices and Technologies*, Vol. 7, pp. 83-93 (1992)), 1,3,4-triazoles (as described by Kido et al. in *Chemistry Letters*, pp. 47-48 (1996)), and dicarboximides of perylene (as described by Yoshida et al. in *Applied Physics Letters*, Vol. 69, pp. 734-736 (1996)).

Polymeric electron-transporting materials in addition to those of the present invention are exemplified by 1,3,4-oxadiazole-containing polymers (as described by Li et al. in *Journal of Chemical Society*, pp. 2211-2212 (1995), by Yang and Pei in *Journal of Applied Physics*, Vol. 77, pp. 4807-4809 (1995)), 1,3,4-triazole-containing polymers (as described by Strukelj et al. in *Science*, Vol. 267, pp. 1969-1972 (1995)), quinoxaline-containing polymers (as described by Yamamoto et al. in *Japan Journal of Applied Physics*, Vol. 33, pp. L250-L253 (1994), O'Brien et al. in *Synthetic Metals*, Vol. 76, pp. 105-108 (1996)), and cyano-PPV (as described by Weaver et al. in *Thin Solid Films*, Vol. 273, pp. 3947 (1996)). The thickness of this layer may be 500 nm or less, preferably 300 nm or less, most preferably 150 nm or less.

The final layer in the electronic device is normally the cathode, which may be formed from any conductive material, preferably a metal. Examples of suitable metals include lithium, calcium, magnesium, indium, silver, aluminum, or blends and alloys of the above. A metallic cathode may be deposited either by thermal evaporation or by sputtering, according to known techniques. The thickness of the cathode may be from 100 nm to 10,000 nm. The preferred metals are calcium, magnesium, indium, and aluminum. Alloys of these metals may also be used. Alloys of aluminum containing 1 to 5 percent of lithium and alloys of magnesium containing at least 80 percent magnesium are highly preferred.

The EL devices of this invention emit light when subjected to an applied voltage of 50 volts or less with luminance efficiency as high as 3.5 Cd/A. If desired, an encapsulating or protecting coating may be applied to one or more exposed surfaces of the finished device.

In a preferred embodiment, the electroluminescent device comprises at least one hole-transporting polymer film and a light-emitting polymer film at least one of which is comprised of a polymer of the invention, arranged between an anode material and a cathode material such that under an applied voltage, holes are injected from the anode material into the hole-transporting polymer film and electrons are injected from the cathode material into the light-emitting polymer films when the device is forward biased, resulting in light emission from the light-emitting layer. In another preferred embodiment, layers of hole-transporting polymers are arranged so that the layer closest to the anode has the lower oxidation potential, with the adjacent layers having progressively higher oxidation potentials. By these methods, electroluminescent devices having relatively high light output per unit voltage may be prepared.

The term "hole-transporting polymer film" as used herein refers to a layer of a film of a polymer which when disposed between two electrodes to which a field is applied and holes are injected from the anode, permits adequate transport of holes into the emitting polymer. The term "light-emitting polymer film" as used herein refers to a layer of a film of a polymer whose excited states can relax to the ground state by emitting photons, preferably corresponding to wavelengths in the visible light range. The term "anode material" as used herein refers to a semi-transparent, or transparent, conducting film with a work function between 4.5 electron volts (eV) and 5.5 eV. Examples are gold and oxides and mixed oxides of indium and tin. The term "cathode material" as used herein refers to a conducting film desirably having a work function between 2.5 eV and 4.5 eV.

It is expressly intended that the foregoing disclosure of preferred or desired, more preferred or more desired, highly preferred or highly desired, or most preferred or most desired substituents, ranges, end uses, processes, or combinations with respect to any one of the embodiments of the invention is applicable as well to any other of the preceding or succeeding embodiments of the invention, independently of the identity of any other specific substituent, range, use, process, or combination.

The following specific embodiments of the invention are especially desirable and hereby delineated in order to provide a detailed disclosure for the appended claims.

1. An arylamine compound of the formula:

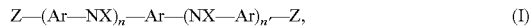

wherein,

Ar independently each occurrence is a group comprising one or more divalent aromatic groups, and optionally two Ar groups separated by a single NX group may be joined together by a second covalent bond or by a bridging group, thereby forming a fused multiple ring system;

X is an inert substituent or a cross-linkable group, with the proviso that in at least one occurrence in said compound, X is a crosslinkable group;

Z independently each occurrence is hydrogen or a leaving group, n is 1 or 2; and n' is 0, 1 or 2.

2. A compound according to embodiment 1 wherein X in at least one occurrence is a moiety containing a double bond, a triple bond, a precursor capable of in situ formation of a double bond, or a heterocyclic, addition polymerizable group.

3. A compound according to embodiment 1 wherein X in at least one occurrence is selected from the group consisting of benzocyclobutanyl groups and substituted $C_{6-12}$ arylene groups containing one or more substituents selected from the group consisting of benzocyclobutane, azide, oxirane, di(hydrocarbyl)amino, cyanate ester, hydroxy, glycidyl ether, $C_{1-4}$ alkylacrylate, $C_{1-4}$ alkylmethacrylate, ethenyl, ethenyloxy, perfluoroethenyloxy, ethynyl, maleimide, nadimide, tri($C_{1-4}$)-alkylsiloxy, tri($C_{1-4}$)alkylsilyl, and halogenated derivatives thereof.

4. A compound according to embodiment 1 wherein X in at least one occurrence is 1-benzo-3,4-cyclobutane or 4-phenyl-1-(benzo-3,4-cyclobutane).

5. A compound according to embodiment 1 wherein Z each occurrence is halo, cyano, triflate, azide, $—B(OR^1)_2$, or

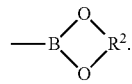

wherein $R^1$, independently in each occurrence, is hydrogen or a $C_{1-10}$ alkyl group, and $R^2$, independently each occurrence, is a $C_{2-10}$ alkylene group.

6. A compound according to embodiment 1 wherein Ar each occurrence is phenylene, 9,9-di($C_{1-20}$alkyl)fluorenyl, or a combination thereof; X is 3,4-benzocyclobutan-1-yl, ethenyl or p-ethenylphenyl; Z is bromine or hydrogen; n is 1 or 2; and n' is 0 or 1.

7. A compound according to embodiment 6 wherein Ar each occurrence is phenylene; each X group is 3,4-benzocyclobutan-1-yl; Z each occurrence is bromine; n is 1 or 2; and n' is 0.

8. A compound according to embodiment 7 wherein n is 1.

9. A compound according to embodiment 1 having the formula:

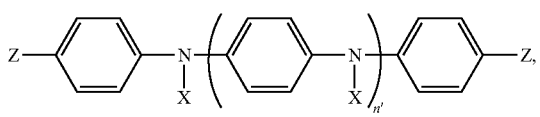
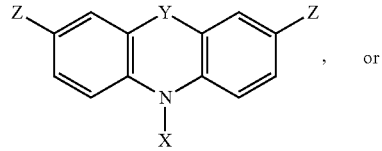
, or

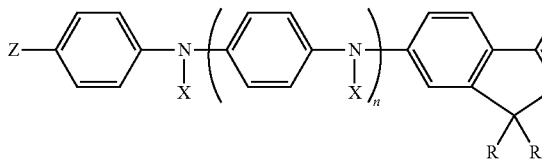
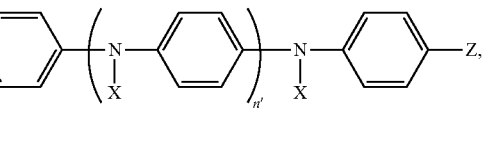

wherein Y is a covalent bond, O, S or NR; where

R independently each occurrence is i) hydrogen; ii) halogen; iii) a $C_{1-20}$ hydrocarbyl group; iv) a hydrocarbyl group substituted with one or more heteroatom containing groups containing up to 20 atoms not counting hydrogen and wherein the heteroatom is selected from S, N, O, P, B or Si; v) a halogenated derivative of iii) or iv); or iv) a substituted derivative of iii) or iv) wherein the substituent is a crosslinkable X group; and n, n', X, and Z are as previously defined in embodiment 1.

10. An oligomer or polymer having one or more repeating groups of the formula:

$$Z'—(Ar—NX')_n—Ar—(NX'—Ar)_n—Z' \quad \text{(Ia)}$$

where X' is X or a divalent crosslinked remnant formed by addition polymerization of a crosslinkable X group;

Z' is Z, a covalent bond, or a terminal group formed by replacement or reaction of a leaving group;

Ar independently each occurrence is a divalent aromatic group, and optionally two Ar groups separated by a single NX group may be joined together by a second covalent bond or by a bridging group, thereby forming a fused multiple ring system;

X is an inert substituent, with the proviso that in at least one occurrence in said compound, X is a crosslinkable group;

Z independently each occurrence is hydrogen or a leaving group, n is 1 or 2; and n' is 0, 1 or 2.

11. An oligomer or polymer according to embodiment 10 having one or more repeating groups Ia) of the formula:

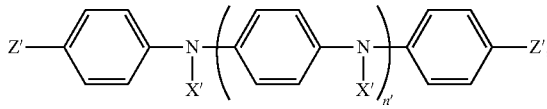
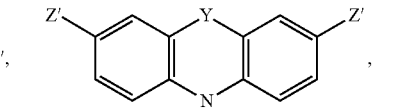
, or

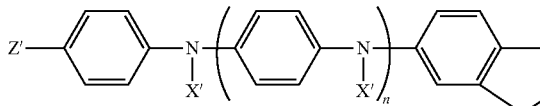
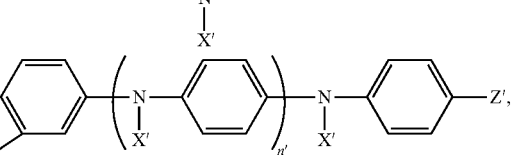

where X' is X or a divalent crosslinked remnant formed by addition polymerization of a crosslinkable X group;

X is an inert substituent or a group capable of forming crosslinking functionality;

Y is O, S or NR';

R independently each occurrence is i) hydrogen; ii) halogen; iii) a $C_{1-20}$ hydrocarbyl group; iv) a hydrocarbyl group substituted with one or more heteroatom containing groups containing up to 20 atoms not counting hydrogen and wherein the heteroatom is selected from S, N, O, P, B or Si; v) a halogenated derivative of iii) or iv); or yl) a substituted derivative of iii) or iv) wherein the substituent is a crosslinkable X group;

Z' is Z, a covalent bond or a terminal group formed by replacement or reaction of a leaving group;

n is 1 or 2; and n' is 0, 1 or 2.

12. A crosslinked polymer according to embodiment 10 or 11 wherein X' in at least one occurrence is a divalent crosslinked remnant formed by addition polymerization of a crosslinkable X group.

13. A crosslinked polymer according to embodiment 12, wherein X' comprises conjugated unsaturation.

14. A process for preparing oligomers or polymers according to embodiment 10, which comprises heating a composition comprising a compound according to embodiment 1 under reaction conditions sufficient to form an oligomer or polymer.

15. A film comprising one or more of the oligomers or polymers according to embodiment 10 or preparable according to embodiment 14.

16. An electronic device comprising one or more layers of polymer films, at least one of which comprises a film according to embodiment 15.

The following examples are included for illustrative purposes only and are not intended to limit the scope of the claims. Unless otherwise stated, implicit from the context or conventional in the art, all parts and percentages herein are based on weight. It is understood that the present invention is operable in the absence of any component which has not been specifically disclosed. The term "overnight", if used, refers to a time of approximately 16-18 hours and "room temperature", if used, refers to a temperature of about 20-25° C.

The following reaction scheme 1 discloses the preparation of a triaryl amine compound with a crosslinkable benzocyclobutane group and its use in a polymerization reaction to make a crosslinkable amine copolymer according to the invention containing 5 mole percent crosslinkable conjugated diaryl amine functionality and 95 mole percent noncrosslinkable diarylamine functional units.

Scheme 1

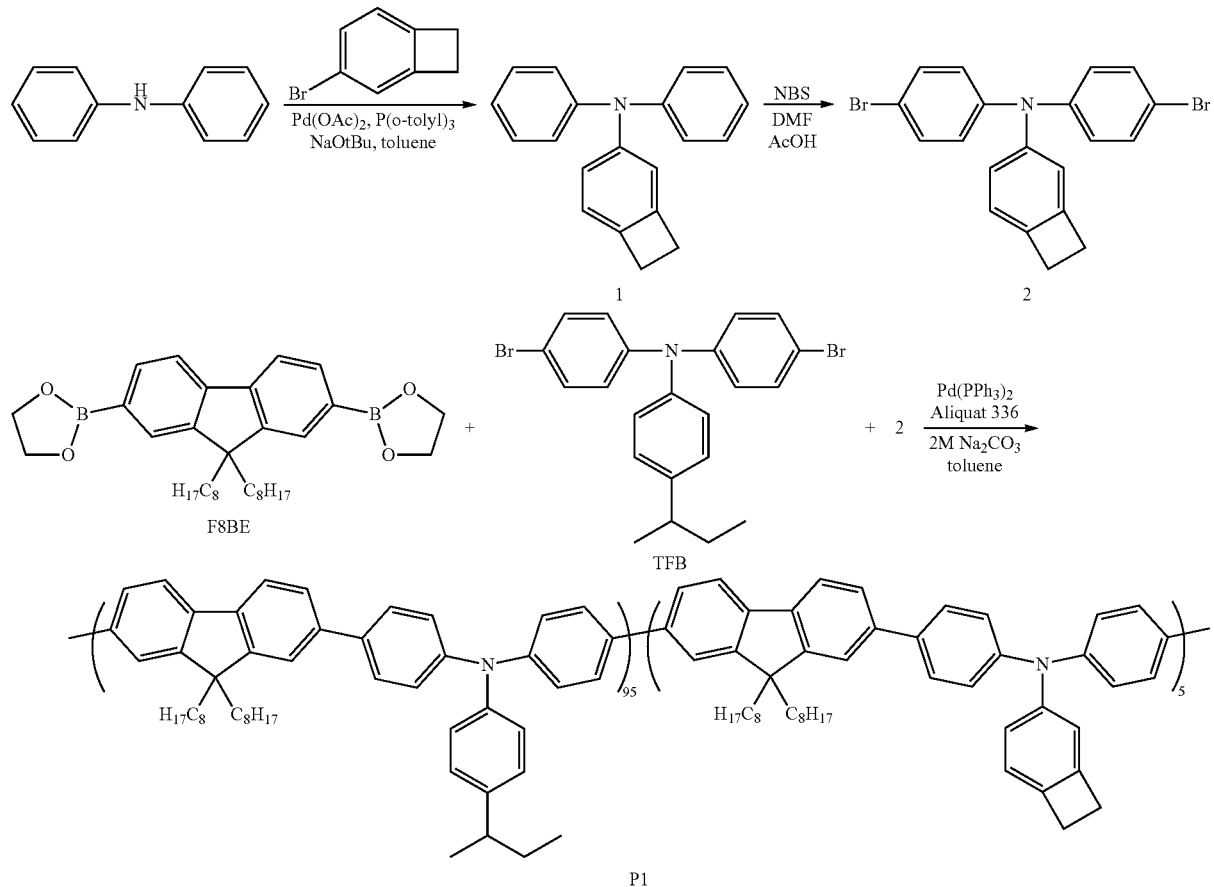

where F8BE is 2,7-bis(1,3,2-dioxyborole)-9,9-di(1-octyl)fluorene and TFB is N,N-di(p-bromophenyl)-N-(4-(butan-2-yl)phenyl)amine.

Example 1

A) Synthesis of diphenyl benzocyclobutane amine (1)

To a 500 ml, 3-neck round bottom flask equipped with a mechanical stirrer, nitrogen inlet, and reflux condenser (with nitrogen outlet), palladium (II) acetate (196 mg, 1.20 mmol) and tri(o-tolyl)phosphine (731 mg, 2.40 mmol) are added to 100 ml toluene. The mixture is stirred at room temperature under nitrogen until the palladium catalyst dissolves and the solution turns yellow. Diphenyl amine (20.0 g, 118 mmol), bromo benzocyclobutane (23.8 g, 130 mmol) and 400 ml toluene are added, followed by sodium t-butoxide (22.8 g, 237 mmol). Upon addition of the sodium t-butoxide the reaction turns black. The reaction is heated to reflux under nitrogen for 22 hours. The reaction is quenched by addition of 30 ml of aqueous 1 M HCl. The toluene layer is washed with 2M $Na_2CO_3$ (100 ml) then the toluene solution is passed through basic alumina. Evaporation of the toluene gives a yellow oil. The product is precipitated by stirring the oil with isopropanol. The solids are collected and recrystallized from hot isopropanol. $^1$H NMR ($CDCl_3$-d) δ: 7.3-6.8 (m, 13H, Ar), 3.12 (d, 4H, —$CH_2CH_2$—).

B) Synthesis of di(4-bromophenyl)benzocyclobutane amine (2)

To a 250 ml round bottom flask, diphenyl benzocyclobutane amine (8.00 g, 29.5 mmol) is added to 100 ml dimethylformamide (DMF) containing 5 drops of glacial acetic acid. To the stirring solution, N-bromosuccinimide (NBS, 10.5 g, 60.7 mmol, 1.97 eq.) is added. After stirring for 5 hours, the reaction is quenched by pouring the reaction mixture into 600 ml of methanol/water (1:1 by vol). A gray solid is recovered by filtration and recrystallized from isopropanol. $^1$H NMR ($CDCl_3$-d) δ: 7.3 (d, 4H, Ar), 7.0 (d, 4H, Ar), 6.95 (t, Ar), 6.8 (s, Ar), 3.12 (d, 4H, —$CH_2CH_2$—).

Example 2

A) Synthesis of Fluorene/Triarylamine Containing Polymer with BCB (P1)

To a 1-liter, 3-neck round bottom flask equipped with reflux condenser and an overhead stirrer, the following monomers are added: F8BE (3.863 g, 7.283 mmol), TFB (3.177 g, 6.919 mmol), and compound 2 (156.3 mg, 0.364 mmol). A 0.74 M toluene solution of a quaternary ammonium chloride catalyst (Aliquat™ 336, available from Sigma-Aldrich Corporation, 3.1 ml) is added followed by 50 ml of toluene. After addition of the $PdCl_2(PPh_3)_2$ catalyst (4.9 mg), the mixture is stirred in an oil bath (105° C.) until all of the monomer is dissolved (about 15 min). An aqueous solution of sodium carbonate (2.0 M, 14 ml) is added and the reaction stirred in an oil bath (105° C.) for 16.5 hours. Phenylboronic acid (0.5 g) is then added and the reaction stirred for 7 hours. The aqueous layer is removed and the organic layer washed with 50 ml of water. The organic layer is placed back in the reaction flask, and 0.75 g of sodium diethyldithocarbamate and 50 ml water are added. The reaction is stirred in an oil bath (85° C.) for 16 h. The aqueous layer is removed, the organic layer is washed with water (3×100 ml) and then passed through a column of silica gel and basic alumina. The toluene/polymer solution is then precipitated into methanol (twice), and the polymer dried under vacuum at 60° C. Yield=4.2 g (82 percent) Mw=124,000; Mw/Mn=2.8.

Example 3

Scheme 2 shows the synthesis of a phenylenediamine monomer with a crosslinkable benzocyclobutane group, and the polymerization reaction used to make a fluorene/amine copolymer containing 5 mole percent of crosslinkable moieties able to achieve conjugated crosslinks.

A) Synthesis of N,N'-diphenyl-N,N'-dibenzocyclobutane-1,4-phenylenediamine (3)

To a 500 ml, 3-neck round bottom flask equipped with a mechanical stirrer, nitrogen inlet, and reflux condenser (with nitrogen outlet), palladium (II) acetate (173 mg, 0.80 mmol) and tri(o-tolyl)phosphine (486 mg, 1.60 mmol) are added to 50 ml toluene. The mixture is stirred at room temperature under nitrogen until the palladium catalyst dissolves and the solution turns yellow. N,N'-diphenyl-1,4-phenylenediamine (10.0 g, 38.4 mmol), bromobenzocyclobutane (15.5 g, 76.8 mmol) and 200 ml toluene are added, followed by sodium t-butoxide (7.37 g, 76.8 mmol). Upon addition of the sodium t-butoxide the reaction turns black. The reaction is heated to reflux under nitrogen for 22 hours. The reaction is quenched by addition of 30 ml of 1 M aqueous HCl. The toluene

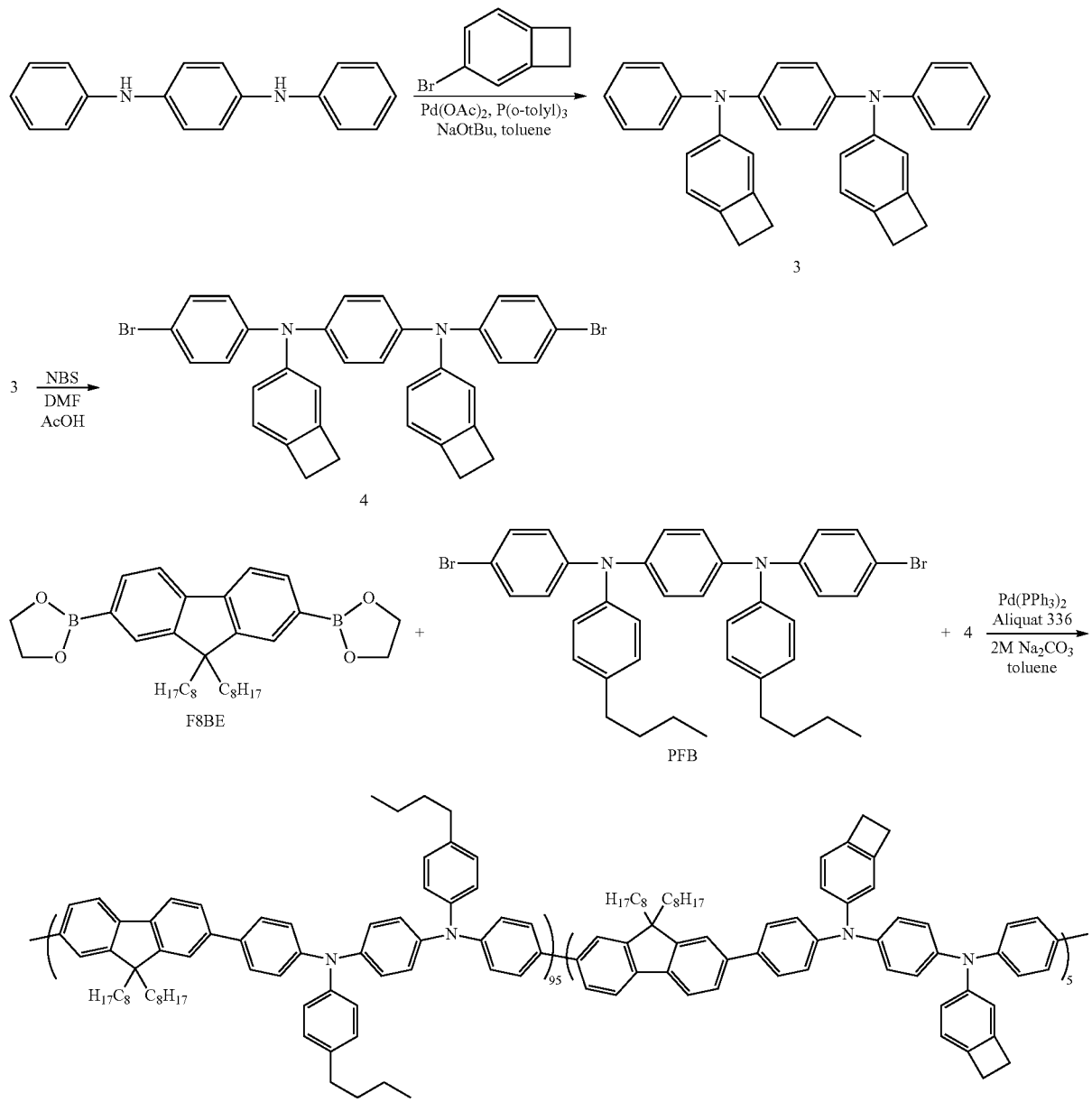

solution is passed through basic alumina and the crude product is purified by recrystallization from a toluene/hexanes/methanol mixture.

Yield=9.43 g (53 percent). $^1$H NMR (THF-d8) δ: 7.15 (t, 4H, Ar), 6.80-7.01 (m, 16H, Ar) 3.09 (s, 8H, —CH$_2$CH$_2$—) $^{13}$C-NMR (THF-d8) δ: 149.72, 148.26, 147.34, 144.18, 141.50, 129.92, 125.82, 125.76, 124.35, 123.61, 122.45, 121.06, 29.78.

B) Synthesis of di(4-bromophenyl)benzocyclobutane amine (4)

To a 500 ml round bottom flask, compound 3 (7.42 g, 16.0 mmol) is added to 200 ml DMF and 150 mL of THF containing 5 drops of glacial acetic acid. To the stirring solution, N-bromosuccinimide (NBS, 5.57 g, 31.5 mmol) is added. After stirring for 18 hours, the product precipitates from the reaction mixture. The product is collected by filtration and recrystallized three times from toluene. Yield=4.44 g (45 percent).

Example 4

Synthesis of fluorene/phenylenediamine polymer containing BCB (P2)

To a 250 mL 3-neck round bottom flask equipped with reflux condenser and an overhead stirrer, the following monomers are added: F8BE (2.922 g, 5.504 mmol), PFB (3.583 g, 5.229 mmol), compound 4 (175 mg, 0.275 mmol), Aliquat™ 336 (available from Sigma-Aldrich Corporation, 0.8 g), and toluene (50 mL). After addition of the PdCl$_2$(PPh$_3$)$_2$ catalyst (3.8 mg), the mixture is stirred in an oil bath (105° C.) until all of the monomer is dissolved (about 15 min). An aqueous solution of sodium carbonate (2.0 M, 12 ml) is added and the reaction stirred while heating in an oil bath (105° C.) for 22 hours. Phenylboronic acid (0.5 g) is then added and the reaction stirred for 24 hours. The aqueous layer is removed and the organic layer washed with water (50 ml). The organic layer is placed back in the reaction flask, and 0.75 g of sodium diethyldithocarbamate and 50 ml water are added. The reaction is stirred in an oil bath (85° C.) for 16 hours. The aqueous layer is removed, the organic layer washed with water (3×100 ml), then passed through a column of silica gel and basic alumina. The toluene/polymer solution is then precipitated into methanol (twice), and the polymer dried under vacuum at 60° C. Yield=3.9 g (78 percent) Mw=61,348; Mw/Mn=2.8.

Example 5

Crosslinked Films

A) The crosslinkable monomers of Examples 2 and 4 are dissolved in 4 ml of mixed xylenes. The solutions are shaken at room temperature overnight and then filtered through a 0.45 μm nylon syringe filter. On a cleaned glass substrate, a cured film of about 80 nm thickness is deposited by spin-coating each solution at 4000 rpm. The films are then heated in a nitrogen-filled oven at 250° C. for 30 min. to create crosslinking in the film. The UV-Vis absorption spectra of the films are measured. The films are then rinsed with toluene, rinsed and dried and the absorption spectra remeasured. Finally, the films are soaked in toluene for 30 minutes, rinsed and dried and the absorption spectra remeasured. Only slight variation in the absorption spectra is observed, indicating that the cured film is essentially unaffected by exposure to toluene.

Figure 2:
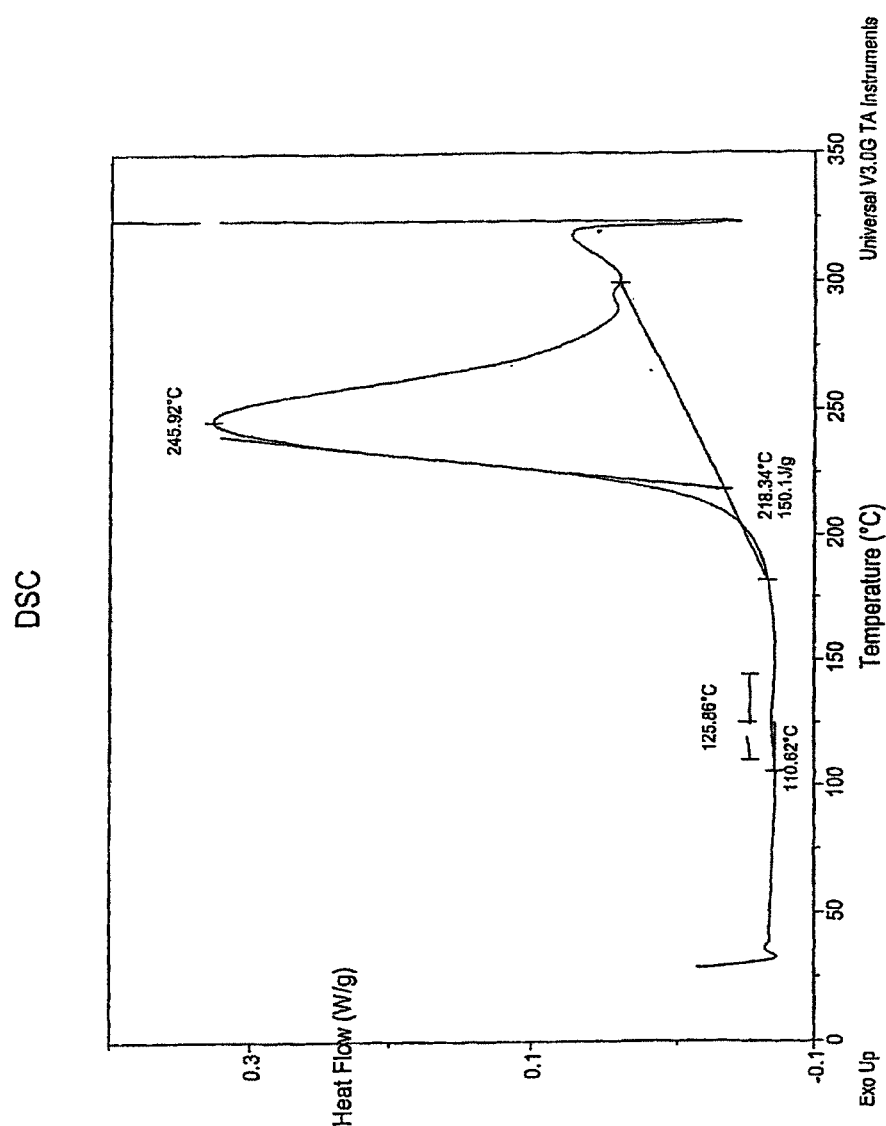
FIGS. 2 and 3 are DSC scans of the compound of Example 3A.
Figure 3:
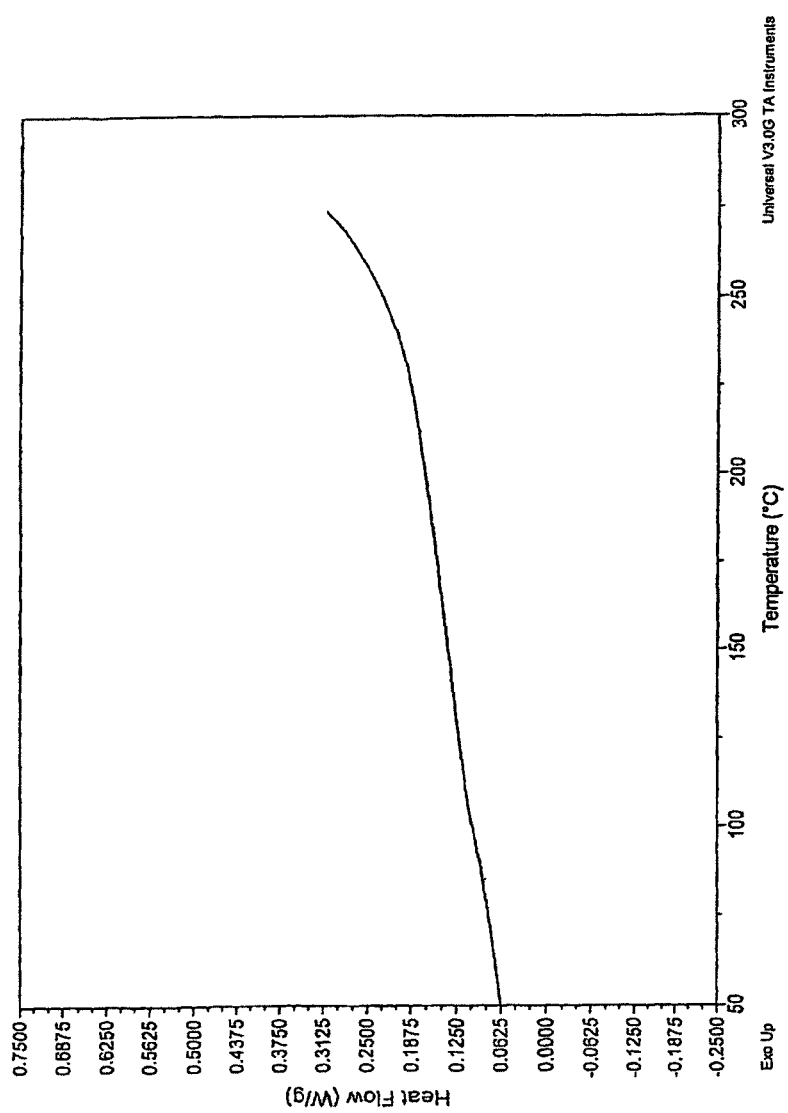

B) A 16.0 mg sample of crosslinkable monomer N,N'-diphenyl-N,N'-dibenzocyclobutane-1,4-phenylenediamine (Example 3A) is analyzed by differential scanning calorimetry (DSC). The initial heating rate is 5° C./min starting from 25° C. to 325° C. In the first heat, (FIG. 2) the compound's melting point is seen at 126° C. and a large exotherm with peak maximum at 246° C. due to the crosslinking reaction between the pendant benzocyclobutane groups is observed. Subsequent heating (FIG. 3) shows the disappearance of both the melting point and the crosslinking exotherm, confirming the formation of a stable crosslinked material has occurred.

Example 6

Light Emitting Device Using Crosslinked and Uncrosslinked Films as Interlayers

A conventional hole transport layer polymer (Baytron P™, available from Sigma-Aldrich Corporation) is spin-coated on a cleaned ITO substrate to a thickness of 80 nm and cured in air at 200° C. for 15 minutes. A filler layer of the crosslinkable polymer from Example 2 is similarly deposited from xylenes (0.5% w/v) and cured (crosslinked) for 30 minutes at 250° C. in a nitrogen atmosphere. Next, a light emitting polymer prepared substantially according to the teachings of U.S. Pat. No. 6,353,083 is spin-coated from a solution in xylenes (1.5% w/v) and cured at a temperature of 130° C. The cathode metals (Ca, 10 nm and Al, 150 nm) are vapor deposited over the resulting polymer film.

The foregoing procedures are substantially repeated to produce light emitting diodes having no interlayer (comparative) and a dried but uncured (uncrosslinked) interlayer. Electroluminescent properties of the light emitting diodes are then tested. Results are reported in FIG. 1.

What is claimed is:

1. An oligomer or polymer having one or more repeating groups of the following formulae:

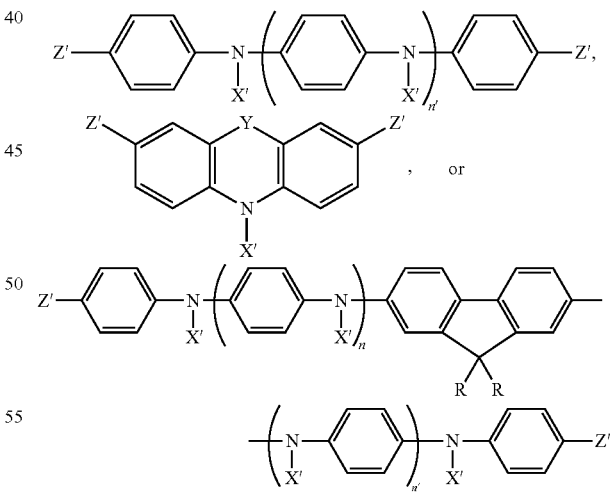

where X' is X or a divalent crosslinked remnant formed by addition polymerization of a crosslinkable X group;

X is an inert substituent or a crosslinkable group represented by any one of the following formulae:
—(R$^4$)$_p$—CR$^3$=CR$^3_2$, —(R$^4$)$_p$—C≡CR$^3$, —(R$^4$)$_p$—O (R$^4$)$_p$ CR$^3$=CR$^3_2$, —(R$^4$)$_p$—O(R$^4$)$_p$ C≡CR$^3$, —(R$^4$)$_p$—CO(R$^4$)$_p$ CR$^3$=CR$^3_2$, —(R$^4$)$_p$—CO(R$^4$)$_p$ C≡CR$^3$, —(R$^4$)$_p$—OC(R$^4$)$_p$ CR$^3$=CR$^3_2$, $-(R^4)_p-OC(R^4)_p$ $C\equiv CR^3$, $-(R^4)_p-OCO(R^4)_p$
$CR^3=CR^3{}_2$, $-(R^4)_p-OCO(R^4)_p$ $C\equiv CR^3$,
$-(R^4)_p-O(CO)O(R^4)_p$ $CR^3=CR^3{}_2$, $-(R^4)_p-O(CO)O$
$(R^4)_p-C\equiv CR^3$, $NR^3{}_2$,

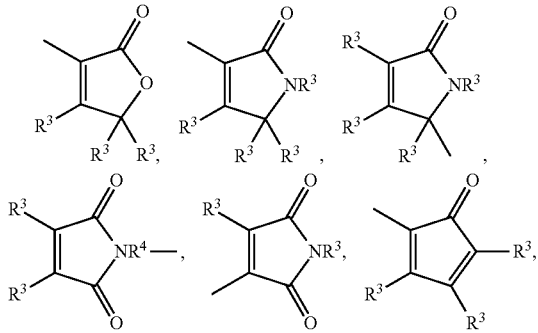

or vi) a substituted derivative of iii) or iv) wherein the substituent is a crosslinkable X group;

Z' independently at each occurrence is hydrogen, a leaving group, a covalent bond, or a terminal group formed by replacement or reaction of a leaving group;

n is 1 or 2; and n' is 0, 1 or 2;

wherein the oligomer or polymer comprises a 9,9-disubstituted fluorenediyl group which may be optionally substituted with one or more substituents.

2. An oligomer or polymer according to claim 1 wherein X in at least one occurrence is 1-benzo-3,4-cyclobutane or 4-phenyl-1-(benzo-3,4-cyclobutane).

3. An oligomer or polymer according to claim 1 comprising:

one or more repeating groups of the following formulae:

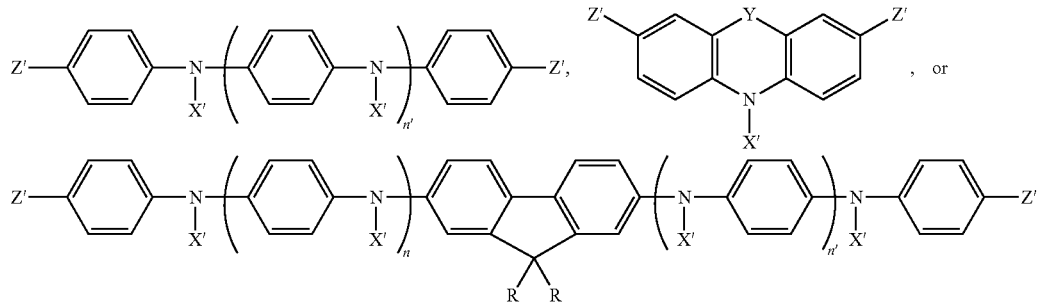

-continued

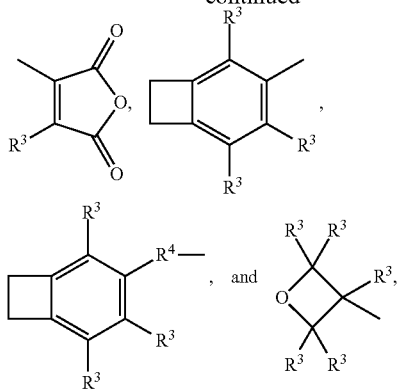

where
$R^3$ is hydrogen, halogen, $C_{1-20}$ hydrocarbyl, $C_{1-20}$ halohydrocarbyl, or $C_{1-20}$ halocarbyl;
$R^4$ is $C_{1-20}$ hydrocarbylene, $C_{1-20}$ halohydrocarbylene, or $C_{1-20}$ halocarbylene; and
p is 0 or 1,
with the proviso that in at least one occurrence in said compound, X is the crosslinkable group;
Y is O, S or NR;
R independently each occurrence is i) hydrogen; ii) halogen; iii) a $C_{1-20}$ hydrocarbyl group; iv) a hydrocarbyl group substituted with one or more heteroatom containing groups containing up to 20 atoms not counting hydrogen and wherein the heteroatom is selected from S, N, O, P, B or Si; v) a halogenated derivative of iii) or iv);

where X' is X or a divalent crosslinked remnant formed by addition polymerization of a crosslinkable X group;

X is an inert substituent or a crosslinkable group represented by any one of the following formulae:

$-(R^4)_p-CR^3=CR^3{}_2$, $-(R^4)_p-C\equiv CR^3$, $-(R^4)_p-O$
$(R^4)_p$ $CR^3=CR^3{}_2$, $-(R^4)_p-O(R^4)_p$ $C\equiv CR^3$, $-(R^4)_p-CO(R^4)_p$ $CR^3=CR^3{}_2$, $-(R^4)_p-CO(R^4)_p$
$C\equiv CR^3$, $-(R^4)_p-OC(R^4)_p$ $CR^3=CR^3{}_2$, $-(R^4)_p-OC(R^4)_p$ $C\equiv CR^3$, $-(R^4)_p-OCO(R^4)_p$
$CR^3=CR^3{}_2$, $-(R^4)_p-OCO(R^4)_p$ $C\equiv CR^3$, $-(R^4)_p-O(CO)O(R^4)_p$ $CR^3=CR^3{}_2$, $-(R^4)_p-O(CO)O$
$(R^4)_p-C\equiv CR^3$, $NR^3{}_2$,

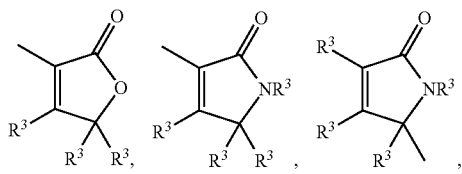

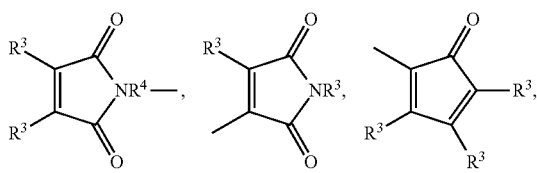

27

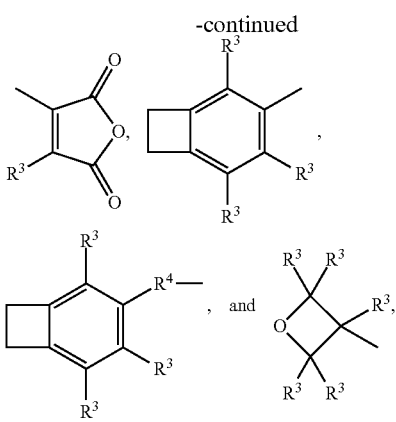

where
R³ is hydrogen, halogen, $C_{1-20}$ hydrocarbyl, $C_{1-20}$ halohydrocarbyl, or $C_{1-20}$ halocarbyl;
R⁴ is $C_{1-20}$ hydrocarbylene, $C_{1-20}$ halohydrocarbylene, or $C_{1-20}$ halocarbylene; and p is 0 or 1,
with the proviso that in at least one occurrence in said compound, X is the crosslinkable group;
Y is O, S or NR;
R independently each occurrence is i) hydrogen; ii) halogen; iii) a $C_{1-20}$ hydrocarbyl group; iv) a hydrocarbyl group substituted with one or more heteroatom containing groups containing up to 20 atoms not counting hydrogen and wherein the heteroatom is selected from S, N, O, P, B or Si; v) a halogenated derivative of iii) or iv); or vi) a substituted derivative of iii) or iv) wherein the substituent is a crosslinkable X group;
Z' independently at each occurrence is hydrogen, a leaving group, a covalent bond, or a terminal group formed by replacement or reaction of a leaving group;
n is 1 or 2; and
n' is 0, 1 or 2;
and from 1 to 99 percent of repeat units of formula:

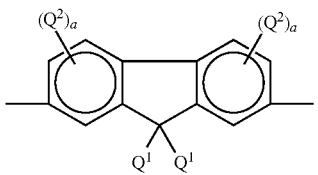

(IIa)

wherein $Q^1$ is independently in each occurrence $C_{1-20}$ hydrocarbyl or $C_{1-20}$ hydrocarbyl containing one or more S, N, O, P, or Si atoms, $C_{4-16}$ hydrocarbyl carbonyloxy, $C_{4-16}$ aryl(trialkylsiloxy) or both $Q^1$ may form

28 with the 9-carbon on the fluorene ring a $C_{5-20}$ ring structure or a $C_{4-20}$ ring structure containing one or more of S, N or O;
$Q^2$ is independently in each occurrence $C_{1-20}$ hydrocarbyl, $C_{1-20}$ hydrocarbyloxy, $C_{1-20}$ thioether, $C_{1-20}$ hydrocarbylcarbonyloxy or cyano; and
a is independently in each occurrence 0 or 1.

4. An oligomer or polymer according to claim 1 wherein the oligomer or polymer is a crosslinked polymer and X' in at least one occurrence is a divalent crosslinked remnant formed by addition polymerization of a crosslinkable X group.

5. An oligomer or polymer according to claim 4, wherein X' comprises conjugated unsaturation.

6. A process for preparing the oligomers or polymers according to claim 1, which comprises heating a composition comprising an arylamine compound of one or more of the following formulae:

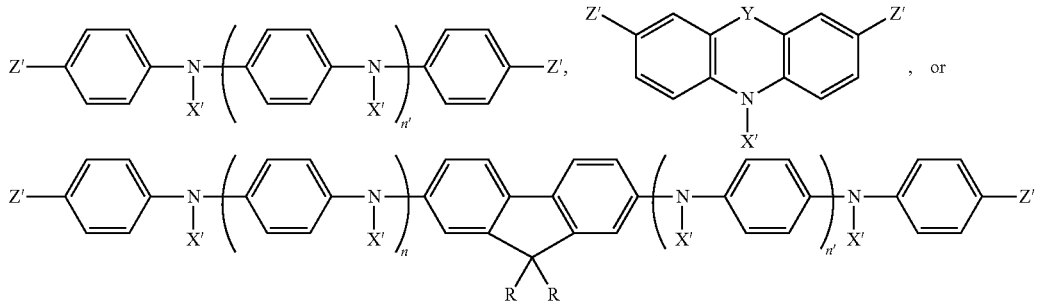

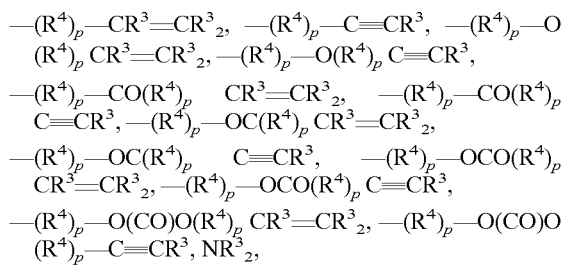

where X' is X or a divalent crosslinked remnant formed by addition polymerization of a crosslinkable X group;

X is an inert substituent or a crosslinkable group represented by any one of the following formulae:

$-(R^4)_p-CR^3=CR^3{}_2$, $-(R^4)_p-C\equiv CR^3$, $-(R^4)_p-O(R^4)_p CR^3=CR^3{}_2$, $-(R^4)_p-O(R^4)_p C\equiv CR^3$, $-(R^4)_p-CO(R^4)_p CR^3=CR^3{}_2$, $-(R^4)_p-CO(R^4)_p C\equiv CR^3$, $-(R^4)_p-OC(R^4)_p CR^3=CR^3{}_2$, $-(R^4)_p-OC(R^4)_p C\equiv CR^3$, $-(R^4)_p-OCO(R^4)_p CR^3=CR^3{}_2$, $-(R^4)_p-OCO(R^4)_p C\equiv CR^3$, $-(R^4)_p-O(CO)O(R^4)_p CR^3=CR^3{}_2$, $-(R^4)_p-O(CO)O(R^4)_p-C\equiv CR^3$, $NR^3{}_2$,

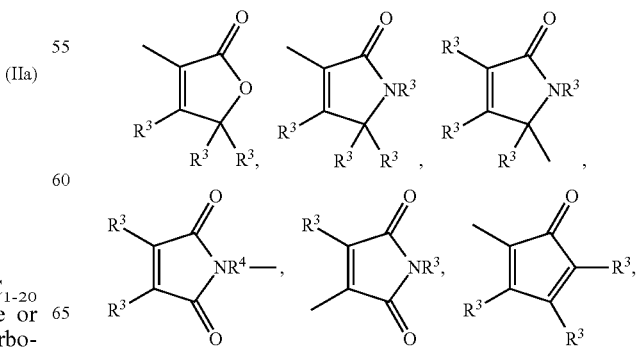

-continued

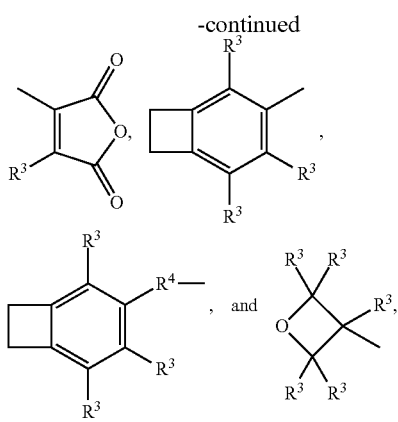
, and
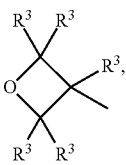

where
R³ is hydrogen, halogen, $C_{1-20}$ hydrocarbyl, $C_{1-20}$ halohydrocarbyl, or $C_{1-20}$ halocarbyl;
R⁴ is $C_{1-20}$ hydrocarbylene, $C_{1-20}$ halohydrocarbylene, or $C_{1-20}$ halocarbylene; and
p is 0 or 1,
with the proviso that in at least one occurrence in said compound, X is the crosslinkable group;
Y is O, S or NR;
R independently each occurrence is i) hydrogen; ii) halogen; iii) a $C_{1-20}$ hydrocarbyl group; iv) a hydrocarbyl group substituted with one or more heteroatom containing groups containing up to 20 atoms not counting hydrogen and wherein the heteroatom is selected from S, N, O, P, B or Si; v) a halogenated derivative of iii) or iv); or vi) a substituted derivative of iii) or iv) wherein the substituent is a crosslinkable X group;
Z' independently at each occurrence is hydrogen, a leaving group, a covalent bond, or a terminal group formed by replacement or reaction of a leaving group;
n is 1 or 2; and
n' is 0, 1 or 2,
under reaction conditions sufficient to form the oligomer or polymer according to claim 1.

7. A film comprising one or more of the oligomers or polymers prepared by the process according to claim 6.

8. An electronic device comprising one or more layers of polymer films, at least one of which comprises a film according to claim 7.

9. A film comprising one or more of the oligomers or polymers according to claim 1.

10. An electronic device comprising one or more layers of polymer films, at least one of which comprises a film according to claim 9.

* * * * *